US009439830B2

(12) United States Patent
Norton

(10) Patent No.: US 9,439,830 B2
(45) Date of Patent: Sep. 13, 2016

(54) TRANSVERSE-MODE-RESONANT STIMULATION DEVICE

(71) Applicant: Bryan Joseph Norton, Seattle, WA (US)

(72) Inventor: Bryan Joseph Norton, Seattle, WA (US)

(*) Notice: Subject to any disclaimer, the term of this patent is extended or adjusted under 35 U.S.C. 154(b) by 281 days.

(21) Appl. No.: 14/160,363

(22) Filed: Jan. 21, 2014

(65) Prior Publication Data

US 2014/0206933 A1 Jul. 24, 2014

Related U.S. Application Data

(60) Provisional application No. 61/755,191, filed on Jan. 22, 2013, provisional application No. 61/758,949, filed on Jan. 31, 2013.

(51) Int. Cl.
*A61F 5/00* (2006.01)
*A61H 23/02* (2006.01)
*A61H 19/00* (2006.01)

(52) U.S. Cl.
CPC .............. *A61H 23/02* (2013.01); *A61H 19/44* (2013.01); *A61H 23/0218* (2013.01); *A61H 2201/5015* (2013.01); *A61H 2201/5048* (2013.01); *A61H 2201/5061* (2013.01); *A61H 2201/5082* (2013.01)

(58) Field of Classification Search
CPC ...... A61H 19/00; A61H 19/30; A61H 19/40; A61H 19/44; A61H 23/02; A61H 23/0218
USPC .................................. 600/38–41; 601/46–97
See application file for complete search history.

(56) References Cited

U.S. PATENT DOCUMENTS

| | | | | |
|---|---|---|---|---|
| 5,263,218 | A | 11/1993 | Giuliani et al. | |
| 8,093,767 | B2 | 1/2012 | Pepin | |
| 8,308,631 | B2 | 11/2012 | Kobashikawa | |
| 8,657,766 | B2 * | 2/2014 | Tuck | A61H 19/44 600/38 |
| 2002/0065477 | A1 * | 5/2002 | Boyd | A61H 19/44 601/47 |
| 2003/0220556 | A1 * | 11/2003 | Porat | A61B 5/0051 600/407 |
| 2005/0275508 | A1 | 12/2005 | Orr et al. | |
| 2008/0174187 | A1 | 7/2008 | Erixon et al. | |
| 2010/0262049 | A1 | 10/2010 | Novak | |
| 2014/0088471 | A1 * | 3/2014 | Leivseth | A63B 23/20 601/89 |
| 2015/0119636 | A1 * | 4/2015 | Yenko | A61H 19/34 600/38 |

* cited by examiner

*Primary Examiner* — John Lacyk
(74) *Attorney, Agent, or Firm* — AEON Law; Adam L. K. Philipp

(57) ABSTRACT

Various embodiments described herein provide a mechanism for transducing transverse vibrational energy into an elastic body of a sexual stimulation device by directly driving the transverse modes of vibration of the elastic body. Additionally, by using an actuator that transduces a force that is proportional to the input current or voltage, the vibration may be driven with any arbitrary waveform.

19 Claims, 11 Drawing Sheets

TRANSVERSE-MODE-RESONANT STIMULATION DEVICE

CROSS-REFERENCE TO RELATED APPLICATIONS

This application claims the benefit of and priority to Provisional Patent Application No. 61/755,191, filed Jan. 22, 2013, titled "Mechanisms and Methods for Coupling Vibrational Energy into Transverse Modes of Elastic Rods and User Feedback Control for Consumer Vibrating Devices" and naming Bryan Joseph Norton as inventor. This application also claims the benefit of and priority to Provisional Patent Application No. 61/758,949; filed Jan. 31, 2013, titled "Mechanisms and Methods for Coupling Vibrational Energy into Transverse Modes of Elastic Rods and User Feedback Control for Consumer Vibrating Devices," and naming Bryan Joseph Norton as inventor. The above-cited applications are hereby incorporated by reference, in their entireties, for all purposes.

BACKGROUND

Tactile sensation can be induced by vibration. The oscillation repeatedly stimulates nerves in the body that are sensitive to mechanical deformation. This is because acoustical waves create periodic stress-strain patterns to which nerves are sensitive. Understanding this, the greater the control the user has over this stress-strain pattern (both spatially and temporally), the more effective a stimulation device can be.

FIG. 2 illustrates a typical prior-art unbalanced-rotary-motor mechanical oscillation transducer 200, such as are commonly employed in vibrating sexual stimulation devices. Rotor 220 rotates about an axis 240 that does not pass through its center-of-mass 230. Because the center-of-mass is some distance 250 from the axis of rotation, a centrifugal force exists during rotation. The force arises from the fact that mass not under the influence of a force moves in a straight line. Because the unbalanced rotor is constrained to move in a circle, a radial force exists. This radial force is dependent on the mass of the rotor, distance from the axis of rotation 240 to the center of mass 230, and the angular velocity of the rotor 210. Using this argument, it is clear that at low angular velocity, only a small amount of energy will be transduced. Driving a harmonic oscillator with such a force makes this consequence even clearer.

Sum of forces in the x direction.

$$M_m\frac{d^2x}{dt^2} + 2\gamma\frac{dx}{dt} + \omega^2 x = M_r l\omega^2\cos(\omega t)$$

Sum of forces in the y direction $$M_m\frac{d^2y}{dt^2} + 2\gamma\frac{dy}{dt} + \omega^2 y = M_r 1\omega^2\sin(\omega t)$$

Solution to the harmonic oscillator equation in the x direction $$x(t) = \frac{M_r 1\omega^2}{M_m Z_m}\cos(\omega t + \varphi)$$

Solution to the harmonic oscillator equation in the y direction $$y(t) = \frac{M_r 1\omega^2}{M_m Z_m}\sin(\omega t + \varphi)$$

Where $Z_m$ is the mechanical impedance and ω is the natural frequency for the oscillator.

$$Z_m = \sqrt{(2\gamma\omega)^2 + (\omega^2 - \omega_0^2)^2}$$

$$\omega_0 = \sqrt{\frac{k}{M_m}}$$

FIG. 3 is a graph 300 showing the amplitude 310 of a prior-art unbalanced-rotary-motor oscillator driven with the frequency dependent force of the motor rotor. As the frequency 305 drops off to zero, so does the amplitude of the response of the rotary-motor oscillator. Unbalanced-rotary-motor oscillators inherently have poor low frequency performance.

Referring again to FIG. 2, the force generated by an unbalanced rotor is dependent only on the mass of the rotor, the distance from the axis of rotation to the center-of-mass 230, and the angular velocity of the rotor 220. The mass of the rotor and distance from the rotation axis are typically dependent on the physical configuration of the device, making them unchangeable during utilization. Only the angular velocity can be changed in application. Unbalanced-rotary-motor-type transducers are incapable of producing vibrations that are more complicated than sinusoids of variable frequency with amplitude that is frequency dependent as described above.

As a result of the nature of rotation, the transduced force is sinusoidal with projections in two dimensions. The two projections have a 90-degree relative phase shift. When an unbalanced-rotary-motor-type oscillator is used to couple energy into the vibrational modes of an elastic object, control over the stimulated modes is limited. Independent of orientation, at least two transverse mode orientations, or one longitudinal and one transverse mode, are stimulated. Energy cannot be coupled into a single transverse orientation. Also, only one frequency can be coupled into the medium at a time.

To improve an unbalanced-rotary-motor oscillator's low frequency performance, only one thing can be done increase the product of the mass of the rotor and the distance it is away from the axis of rotation, both of which increase the moment of inertia of the rotor. This has two undesirable consequences: increasing the size of the device and decreasing the rate at which the oscillator can change frequencies. Another fundamental limitation exists with the unbalanced-rotary-motor-type oscillator. It is born of the fact that the amplitude of the oscillation and its frequency have a fundamental link, discussed earlier. This does not produce the necessary control required for arbitrary waveform transduction.

Many applications exist that require or could benefit from the independent control of the amplitude of the oscillation and its frequency.

DESCRIPTION

Figure 1:
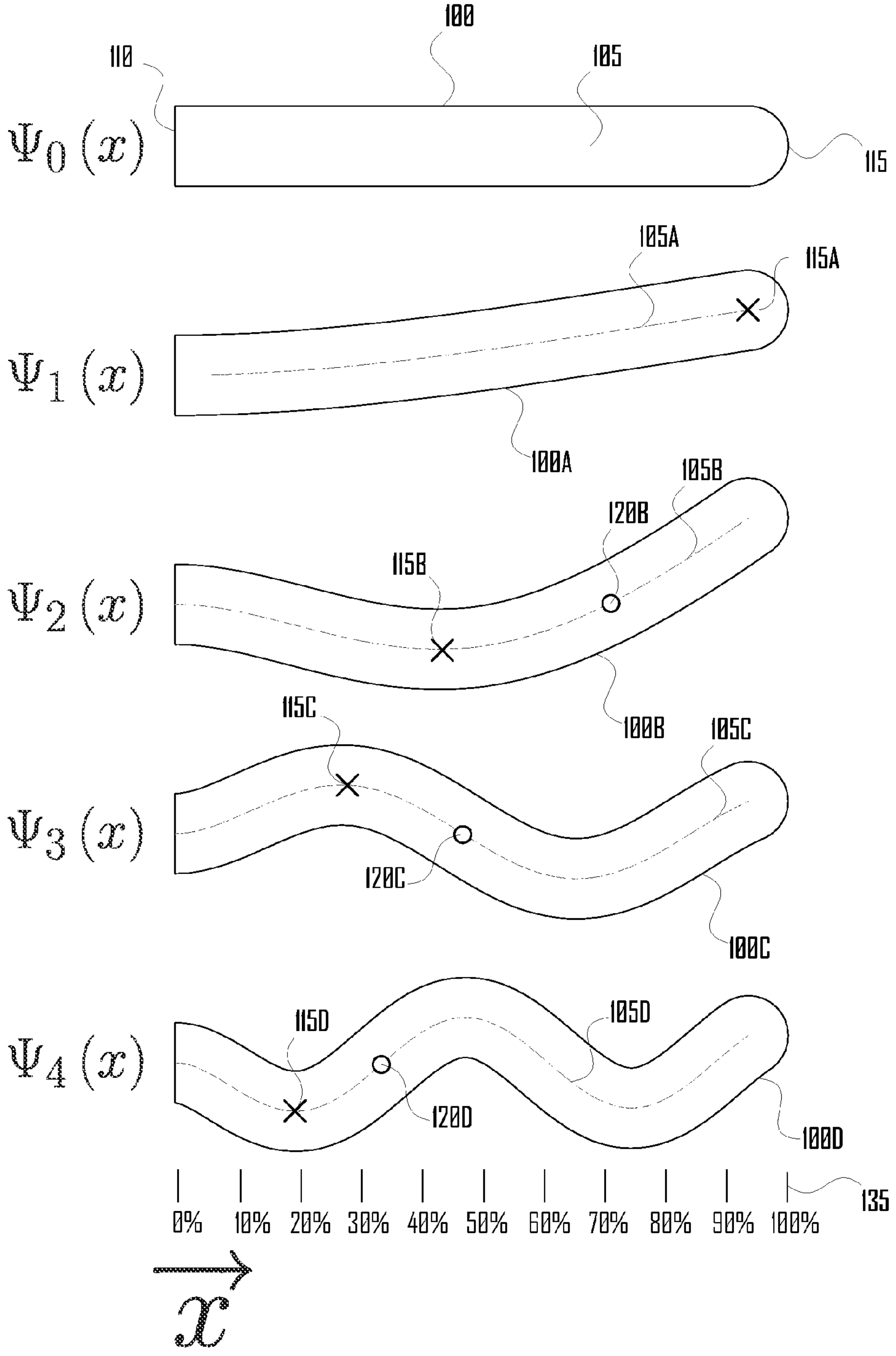
FIG. 1 shows a graphical representation of an elastic rod and its first four normal transverse modes.
Figure 2:
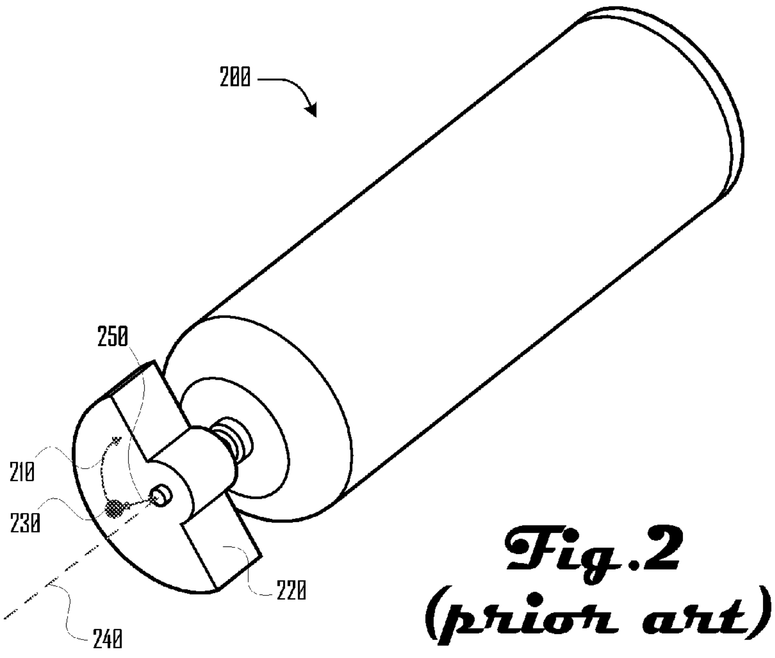
Fig.2 (prior art)
FIG. 2 shows a prior art mechanical oscillation transducer.
Figure 3:
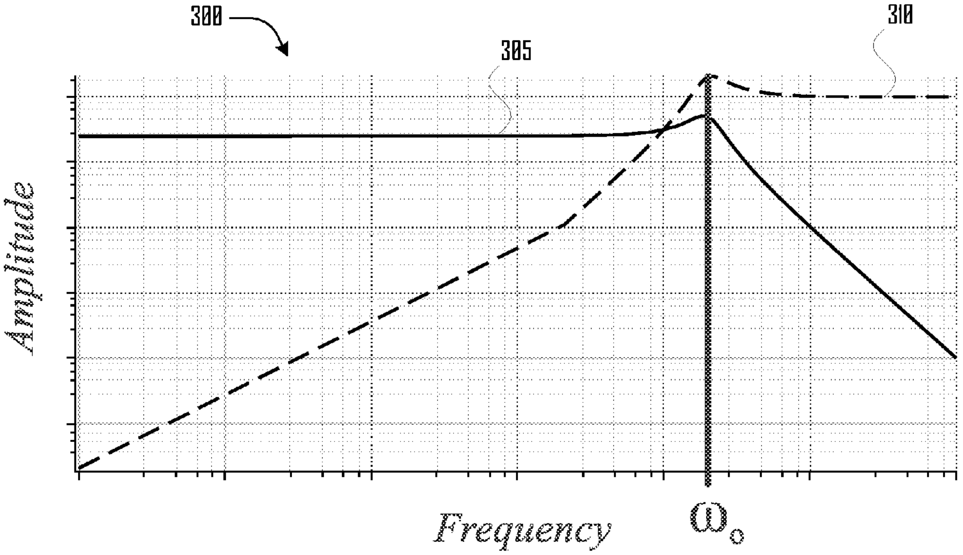
Fig.3 (prior art)
FIG. 3 shows the amplitude of a prior-art oscillator driven with the frequency dependent force of the motor rotor and the amplitude of an oscillator driven by a force independent of the driving frequency.

The function of a sexual stimulation device is to create a tactile sensation perceived by the user. Humans typically perceive tactile vibrations in a limited frequency band of about 0.1 Hz-1 kHz. Vibration perception thresholds measured in human subjects are dependent on frequency. The relationship between perception and frequency has a U shape with the lowest threshold at 150-200 Hz and increases dramatically for frequencies over ~400 Hz. Ideally, a stimulation device would have the capability to generate vibration above the perception threshold across the perception band.

Another consideration is the resonant structures of the body. Most soft tissue in the body resonates at low frequencies (5-10 Hz). Targeting the resonant frequencies of biological structures has the benefit of resulting in larger oscillation amplitudes than the device alone could achieve.

To efficiently transfer waves to the user's body, stimulation devices are commonly made of a material with mechanical properties similar to that of the target body. For example, elastomer with a Young's modulus close to that of soft tissue is conventionally used.

Elastic media supports three distinct types of wave motion: longitudinal, transverse, and torsional. For a rod such as those typically employed as a stimulation device, both longitudinal and torsional waves have a first resonant mode that is outside the perception band. Only transverse waves support modes low enough in frequency to provide good performance.

Coupling energy from one medium to another is dependent on the boundary condition between the two mediums. In the case of acoustical energy in an elastic medium, displacement for the boundary is required. Longitudinal waves compress the medium in the axial direction leading to small displacement at the tissue-device boundary. Similarly, torsional waves twist the medium around the rod's axis, which also leads to small displacement at the tissue-device boundary. By contrast, transverse waves produce a pattern of displacement perpendicular to the length of the device. This leads to significant displacement of the device boundary. The tissue is in contact with the device along its length, coupling vibrational energy into the body.

Theoretical Background for Transverse Modes on an Elastic Rod

To illustrate the behavior of interest, an elastic body of cylindrical shape is a good model.

The wave equation for transverse modes in a rod:

$$\frac{\partial^4 \Psi(x,t)}{\partial t^4} = -\frac{\rho}{Ek^2}\frac{\partial^2 \Psi(x,t)}{\partial t^2}$$

Where:

E is Young's modulus k is the second moment of area p is the density of the medium $\Psi$(x, t) is the displacement of the rod from equilibrium $$\Psi(x,t)=\Psi(x)e^{i\omega t}$$

Separating space and time:

$$\Psi(x)=Ae^{i\gamma x}+Be^{-i\gamma x}+Ce^{\gamma x}+De^{-\gamma x}$$

The above assumption allows for the spatial modes to be solved for, independent of time.

Where:

$$\gamma = \left(\frac{4\pi^2 v}{Ek^2}\right)^{\frac{1}{4}}$$

and A, B, C, D are constants

Applying boundary conditions to each end of the rod constrains the mode shape. The left end of the rod is fixed in displacement and slope. The right end of the rod is free having no torque or force acting on it.

| | Left end of rod | Right end of rod | |
|---|---|---|---|
| Zero displacement | $\psi(0) = 0$ | $\frac{\partial^2 \psi(1)}{\partial t^2} = 0$ | Zero torque (free end) |
| Zero slope | $\frac{\partial \psi(0)}{\partial t} = 0$ | $\frac{\partial^3 \psi(0)}{\partial t^3} = 0$ | Zero force (free end) |

The above conditions result in a set of vibrational modes that characterize the shape of the rod during oscillation. Each mode has a characteristic shape corresponding to a resonant frequency. The order of the mode is denoted by n. where n=1, 2, 3, . . . .

$$\Psi_n(x) = a_n\left(\cosh\left(\frac{\pi\beta_n x}{l}\right) - \cos\left(\frac{\pi b_n x}{l}\right)\right) + b_n\left(\sinh\left(\frac{\pi b_n x}{l}\right) - \sin\left(\frac{\pi b_n x}{l}\right)\right)$$

$$b_n = a_n\frac{\cosh(\pi b_n)+\cos(\pi b_n)}{\sinh(\pi b_n)+\sin(\pi b_n)} = a_n\frac{\sinh(\pi b_n)-\sin(\pi b_n)}{\cosh(\pi b_n)+\cos(\pi b_n)}$$

This also leads to a set of allowed frequencies corresponding to the modes of oscillation.

$$f_n = \frac{\pi}{2l^2}\sqrt{\frac{Qk^2}{r}}\,\beta_n^2$$

Where:

$$\beta_1=0.597, \beta_2=1.494, \beta_3=2.500, \beta_n=(n-½)$$

FIG. 1 shows a graphical representation of the elastic rod 100 where n=0 represents its static state and normal transverse modes for n=1, 2, 3, 4. Elastic rod 100 may be suitable for use as an elastic-body component of a sexual stimulation device in accordance with various embodiments. Although elastic rod 100 is depicted as a featureless circular cylinder with a squared proximal end 110, a rounded distal end 115, and a length to width proportion of almost 8:1, elastic bodies used in other embodiments may be molded to include various textures, protrusions, or other surface features such as are commonly employed in devices designed for internal and/or external stimulation of a human sexual orifice. Similarly, other embodiments may vary from the proportions of elastic rod 100, and some embodiments may have a non-circular and/or varying cross section. Although many embodiments may employ a generally rod-shaped or cylindrical elastic body, some embodiments may be curved when in a static state. Elastic rods 100 and 100*a-d* also have longitudinal axes 105 and 105*a-d* (shown in broken lines) that follow a cross-sectional centroid along the long axis of the body. Some embodiments may vary in width and/or girth along their longitudinal axes.

Elastic rod 100*a* depicts the fundamental transverse mode of vibration (n=1). This mode corresponds to the first resonant frequency of the rod system. For mechanical properties appropriate for use as a stimulation device, the first resonance is around 12 Hz. Elastic rods 100*b*, 100*c*, and 100*d* represent the next three modes n=2, 3, 4 with resonances of 76 Hz, 212 Hz, and 416 Hz respectively. This shows that transverse modes are well suited for this application supporting both low frequency modes and significant displacement along the length of the device. In the case that two orthogonal transverse modes are excited in phase, it can be shown that the resultant displacement is equivalent to a single transverse mode at some angle relative to the two orthogonal modes.

As illustrated, elastic rods 100*a-d* are deformed into mode shapes corresponding respectively to modes n=1, 2, 3, 4 such as may be the case when elastic rods 100*a-d* are mechanically resonating at resonant frequencies 12 Hz, 76 Hz, 212 Hz, and 416 Hz, respectively. When elastic rods 100*a-d* are resonating in such modes of vibration, a standing wave may result, which is characterized by one or more nodes (points where the wave has minimum amplitude), such as nodes 120B-D, and anti-nodes (points where the wave has maximum amplitude), such as anti-nodes 115A-D. (FIG. 1 illustrates only the nodes and anti-nodes that are closest to the fixed, proximal (left) end of elastic rods 100*a-d*.) Body-length scale 135 roughly marks distances from the fixed, proximal (left) end of elastic rods 100*a-d* as percentages of the overall length of elastic rod 100.

Various embodiments described herein provide a mechanism for transducing transverse vibrational energy into an elastic body of a sexual stimulation device by directly driving the transverse modes of vibration of an elastic body or rod. Additionally, by using an actuator that transduces a force that is proportional to the input current or voltage, the vibration may be driven with any arbitrary waveform. In some embodiments, the device may be able to faithfully reproduce any arbitrary waveform within the bandwidth of the device.

Figure 4:
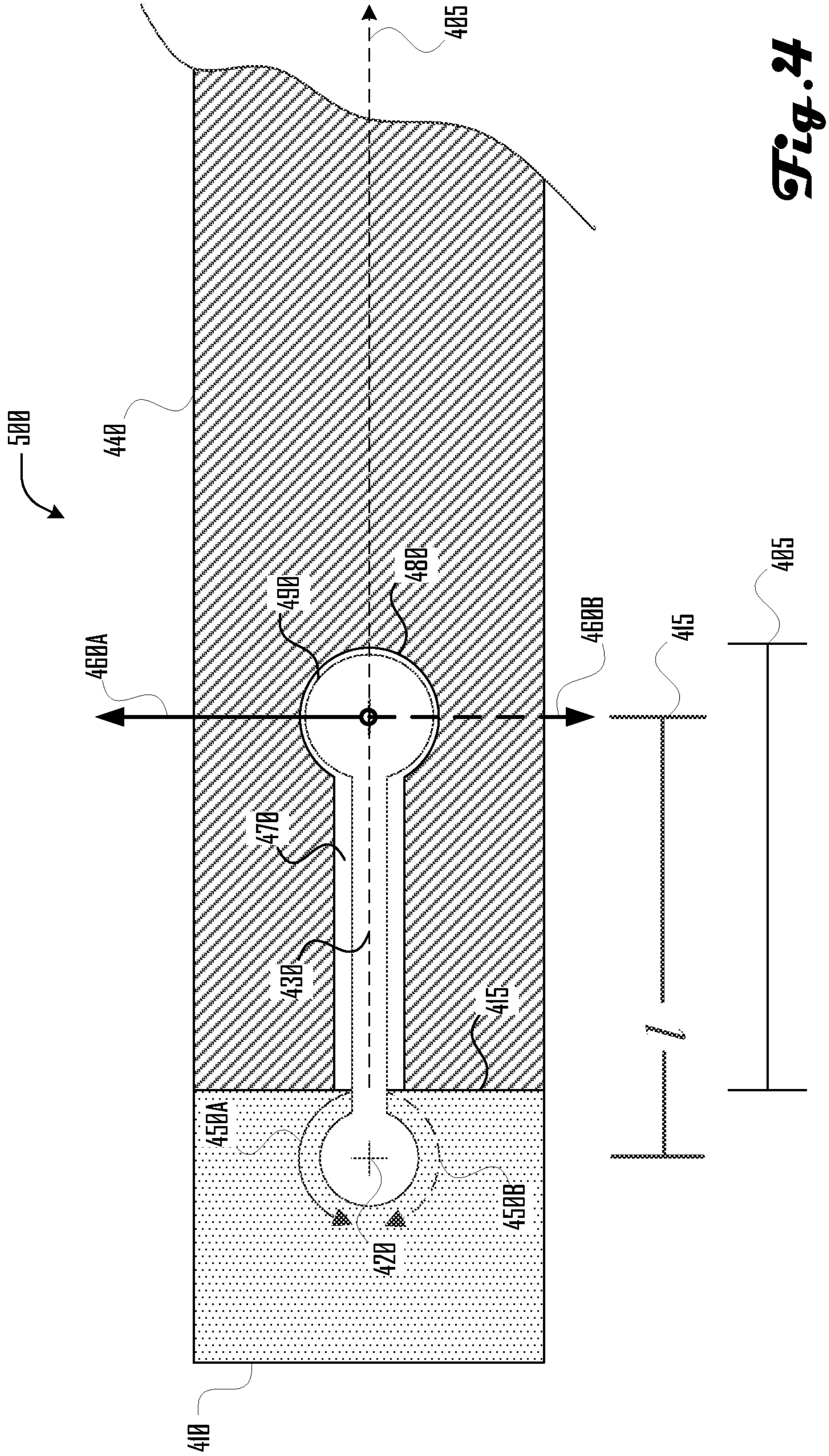
FIGS. 4-6 depict various torque-transducer stimulation devices, in accordance with various embodiments.

FIG. 4 depicts base-torqued torque transducer 400, in accordance with one embodiment. Torque transducer 400 comprises elastic body 440 and actuator 410. Actuator 410 comprises a transverse pivot 420 and an actuator arm or rotor arm 430 that pivots about pivot 420. Transverse pivot 420 is oriented transverse to a longitudinal axis 405 of elastic body 440. Actuator 410 abuts a proximal end 415 of elastic body 440 and, when driven by an appropriate input current, generates a torque 450*a* around transverse pivot 420, resulting in a rotation of arm 430 about pivot 420, imparting transverse force 460*a* into the elastic body 440. Actuator 410 can also generate a counterclockwise torque 450*b*, resulting in transverse force 460*b*.

Both the torque and the force can be reversed so that, in the diagram, both force 460*a* and torque 450*a* can be in the opposite direction as depicted in force 460*b* and torque 450*b*. When driven by a suitable input current, actuator 410 may periodically alternate between generating torques 450*a* and 450*b* so as to generate an oscillating force that is imparted into elastic body 440 via the distal end 490 of rotor arm 430, which is mechanically coupled with internal drive surface 480 of elastic body 440, as discussed below.

Elastic body 440 also includes a hollow bore 470 extending along longitudinal axis 405. Rotor arm 430 projects through hollow bore 470, which allows elastic rod 440 to move somewhat independently of rotor arm 430. The distal end 490 of rotor arm 430 is mechanically coupled with an internal drive surface 480 of elastic body 440. In some embodiments, rotor arm 430 is not coupled with other interior surfaces of hollow bore 470 except at distal end 490. In other embodiments, other portions of rotor arm 430 may be in contact with other interior surfaces of hollow bore 470. In some embodiments, the distal end of rotor arm 430 is rigidly coupled with internal drive surface 480. In other embodiments, the distal end of rotor arm 430 may be non-rigidly coupled such that elastic body 440 may rotate about its longitudinal axis relative to rotor arm 430. In the illustrated examples, hollow bore 470 does not extend beyond internal drive surface 480. In other embodiments, hollow bore may extend beyond internal drive surface 480.

The distance (l) 415 between pivot 420 and the distal end 490 of rotor arm 430 is chosen to correspond to the maximum displacement of the highest mode in which the device is designed to operate. For considering the optimal length for the actuator arm, an expression describing displacement of the elastic body can be derived.

$$\psi(x, y) = \frac{2}{\rho A l_T} \sum_{n=1}^{\infty} \frac{Y_n(l) Y_n(x)}{\omega_n} \left[ \frac{\omega \sin(\omega t) - \omega_n \sin(\omega_n t)}{\omega_n - \omega_n^2} \right]$$

Where:

$\psi_n(x)$ describes the normal modes of the elastic rod subject to boundary conditions;

A is the cross sectional area of the rod;

$l_T$ is the total length of the rod;

Y is displacement of the rod resulting from multiple modes; and $\omega_n = 2\pi f_n$.

The mode shape plays an important role in the placement of the driving force and subsequently the length of the arm. As can be seen from the above expression, the amplitude of the response is proportional to the particular mode being driven evaluated at the driving location l. If l is placed at a node of a mode, then that mode will not be stimulated. Conversely, the closer to the anti-node of a given mode l is placed, the better coupling into that mode will be achieved. To optimize coupling into a set of modes a compromise length is found, as discussed further below.

The projection distance 405 (measured from the proximal end of elastic body 440 to internal drive surface 480) is a function of distance (l) 415. For example, referring back to FIG. 1, if elastic rod 100 were designed to be excited to resonate in modes of vibration where n is equal to 4, projection distance 405 may be selected to position internal drive surface 480 near anti-node 115D (corresponding to the fourth mode of vibration) and/or between anti-node 115D and node 120D.

In the case that multiple modes are to be stimulated, that distance is chosen to be a compromise between that set of modes. For example, if elastic rod 100 were designed to be excited to oscillate in modes of vibration where n is less than or equal to 4, projection distance 405 may be selected to position internal drive surface 480 near node 115D and/or between node 115D (corresponding to the fourth mode of vibration) and node 115C (corresponding to the third mode of vibration).

More generally, in many embodiments, projection distance 405 may be selected to extend between 20% to 25% of the body length of an elastic body. Other embodiments may employ longer or shorter projection distances. For example, if elastic rod 100 were designed to be excited to oscillate in modes of vibration where n is less than or equal to 3, projection distance 405 may be selected to extend between 25% to 40% of the body length. Most embodiments will employ a projection distance of less than 50% of the body length.

Torque transducer 400 couples mechanical energy into a set of transverse modes of elastic rod 440. It is coupling energy into a single transverse orientation by creating a force that is transverse to the longitudinal axis 405, which distorts the rod into the desired mode shape. Because the force is transferred directly into the elastic body, static deformation of the elastic rod is supported. As a result, the full bandwidth of the actuator is coupled to the rod. If an appropriate actuator is chosen to drive this device, the full bandwidth of interest (0.1 Hz-1 kHz) can be utilized.

Figure 5:
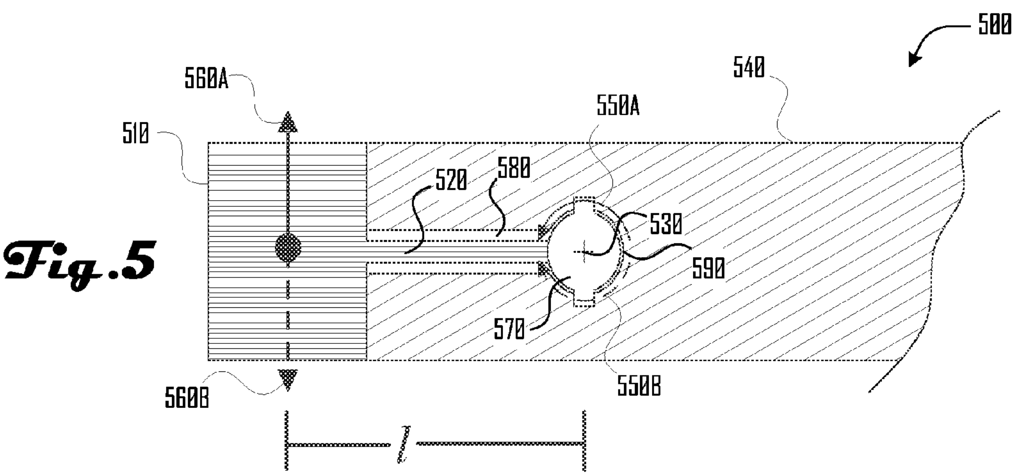

FIG. 5 depicts mid-torqued torque transducer 500, in accordance with one embodiment. Torque transducer 500 comprises an actuator body 510, rigid arm 520, pivot 530, and an elastic rod 540. The actuator 510 creates a torque 550*a* around pivot 530 resulting in a rotation of rotor 570 about pivot 530. Elastic rod 540 includes a hollow bore 580 through which arm 520 projects, allowing elastic rod 540 to move somewhat independently of the arm 520. Rotor 570 and elastic rod 540 are in contact along the internal drive surface 590. As discussed above, the distance (L) between pivot 570 and actuator body 510 is chosen to maximize the coupling of energy into the desired modes. Pivoting rotor 570 forms a node of displacement and an anti-node of rotation. Note that actuator body 510 is free to move about pivot 530, which leads to displacement at the end of the device as a result of force 560*a*. Both the torque and the force can be reversed so that both force 560*a* and torque 550*a* can be in the opposite direction as depicted in FIG. 5.

Torque transducer 500 couples mechanical energy into a single transverse mode of elastic rod 540 by creating a torque that twists the elastic medium about an axis transverse to the length of the rod, which distorts the rod into the desired mode shape. Because the torque is transferred directly into the elastic body, static deformation of the elastic rod is supported. As a result, the full bandwidth of the actuator is coupled to elastic rod 540. If an appropriate actuator is chosen to drive this device, the full bandwidth of interest (0.1 Hz-1 kHz) can be utilized.

Figure 6:
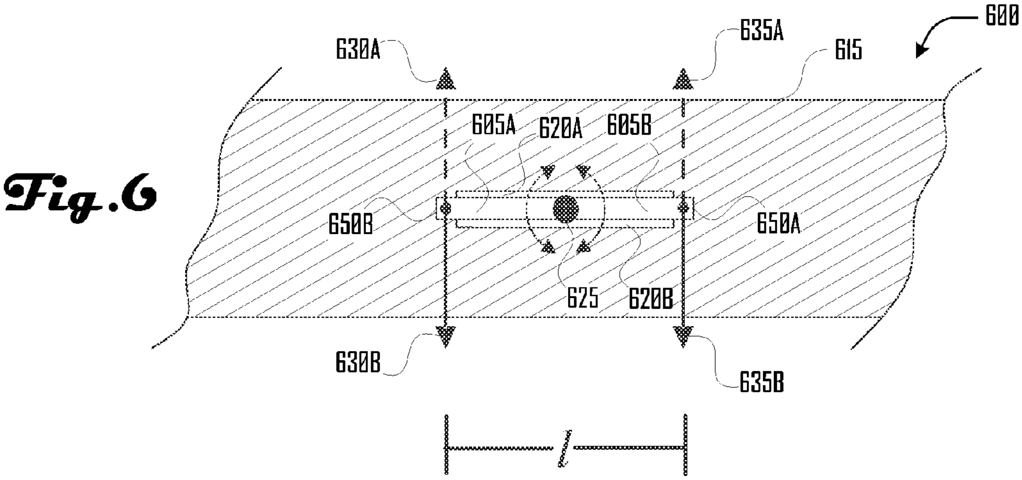

FIG. 6 depicts a torque transducer 600, in accordance with one embodiment. Torque transducer 600 is comprised of two opposing rotors 605*a* and 605*b*, pivot 625, and an elastic rod 615.

A torque is created on rotor 605*a* relative to the second rotor 605*b* around pivot 625 resulting in a rotation about pivot 625. Elastic rod 615 includes hollow bores 620*a* and 620*b* between actuator rotors 605*a* and 605*b* and the elastic rod 615. Hollow bores 620*a* and 620*b* allow elastic rod 615 to move somewhat independently of the actuator rotors 605*a* and 605*b*.

Actuator rotors 605*a* and 605*b* and elastic rod 615 are in contact along the boundaries 650*a* and 650*b*, respectively. In other embodiments, both the torques can be reversed so that, in the diagram, torques 635*a* and 630*a* can be in the opposite direction as depicted by torques 635*b* and 630*b*.

The distance (L) between the respective ends of actuator rotors 605*a* and 605*b* is chosen to maximize the coupling of energy into the desired modes. In this configuration, pivot 625 is a displacement node and an anti-node of rotation.

Torque transducer 600 couples mechanical energy into a single transverse mode of elastic rod 615 by creating a torque that twists the elastic medium about an axis transverse to the length of the rod, which distorts the rod into the desired mode shape. Because the torque is transferred directly into the elastic body, this device supports static deformation of the elastic rod. As a result, the full bandwidth of the actuator is coupled to the rod. If an appropriate actuator is chosen to drive this device, the full bandwidth of interest (0.1 Hz-1 kHz) can be utilized.

In various embodiments, sexual stimulation devices utilizing torque transducers such as 400, 500, and 600 can be driven with rotary voice coil actuators. The efficiency of such actuators is characterized by the so-called Bl product. The Bl product is the length of the actuator's coil multiplied by the strength of the magnetic field to which it is subject. The Bl product is also the quantity that relates the coil current and the resultant force (F=(Bl)i). The larger the Bl product, the more efficient the actuator $$\left(\frac{1}{\eta} = 1 + \frac{2Rm\xi}{(Bl)^2}\right).$$

Moving coil actuators have an inherent limitation that the coil must be in between the two magnets. Restricting the length of the actuator coil, if the gap width is increased to fit a wider coil, the magnetic field in the gap decreases. For a given magnet width, there exists a maximum efficiency gap width. This is an inherent limitation of moving coil actuators. One way to improve this limitation is to reverse the roles of the coil and the magnet with a moving magnet actuator design.

Figure 7A:
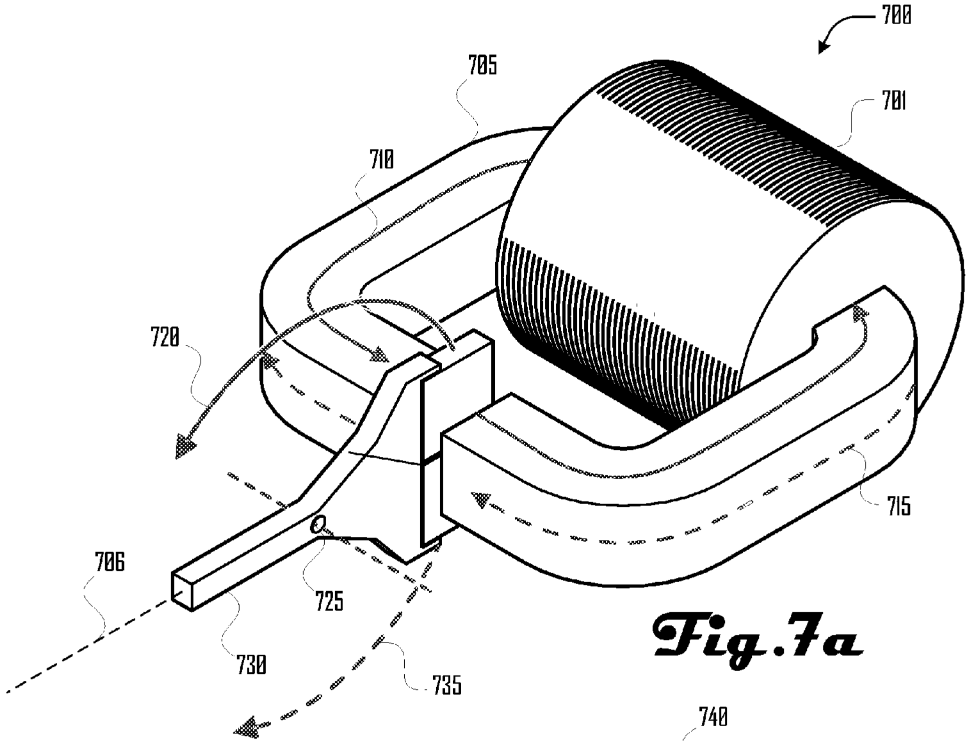
FIGS. 7$a$-$c$, 9-10, 11$a$-$b$, 12$a$-$c$, and 13-14 depict various rotary moving-magnet actuator designs, in accordance with various embodiments.
Figure 7B:
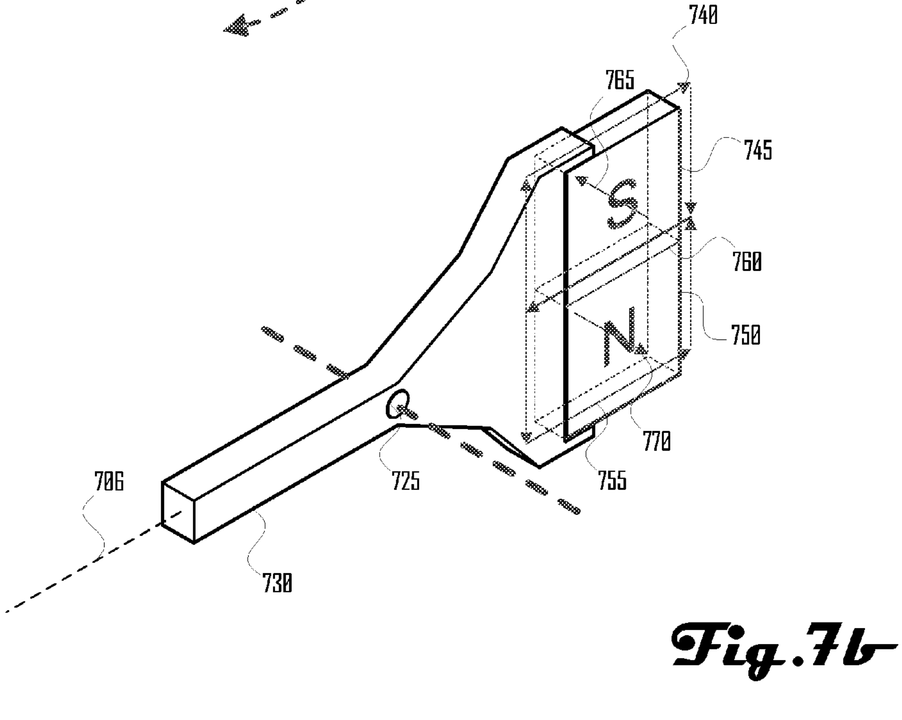
Figure 7C:
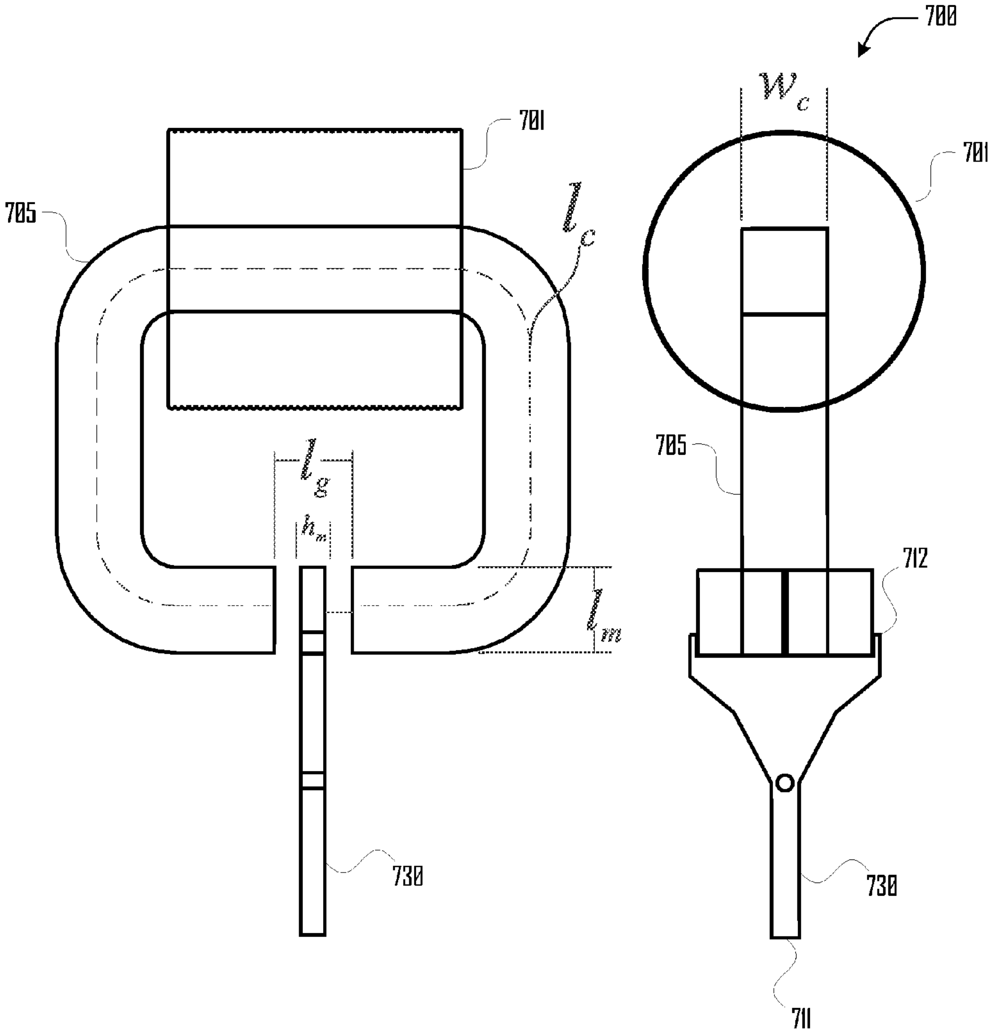

FIGS. 7*a-c* depict a rotary moving-magnet voice-coil actuator 700 such as may be used as the actuator in torque transducers 400 and/or 500, as discussed above, in accordance with one embodiment. Actuator 700 comprises a core 705 of low magnetic-reluctance material; pivot 725; rotor arm 730; coils 701; and magnets 745 and 750. In some embodiments, such a moving-magnet actuator may be adapted for use as an actuator in torque transducer 600, as discussed above.

The "C" shaped core 705 carries the magnetic field created by the coil 701 to gap lg creating a magnetic field that is proportional to the current in the coil 701. The pivot assembly consists of a rotor arm 730; a pivot 725, which has a proximal end 712 and a distal end 711 and is oriented transverse to a longitudinal axis 706 of an elastic body (not shown); and two magnets 745 and 750 at the proximal end 712. The magnetic fields for permanent magnets are oriented in opposite directions as depicted by vectors 765 and 770.

Permanent magnets can be described in two equivalent ways: the magnetization of the bulk material or the equivalent surface current around the edge of the magnet as depicted by arrows 740 and 755. Because the two magnets are arranged with their magnetic fields 710 (counterclockwise field) and 715 (clockwise field) in opposite directions, the equivalent surface current 740 and 755 adds together on the edge 760 that the magnets are in contact. The common edge 760 of the magnets is held in the center of the core gap lg by the pivot 725.

In one embodiment, magnets 745 and 750 may be permanent rare-earth magnets, such as neodymium magnets. Because neodymium magnets have such a large remnant magnetization, the surface current is large (~1 kA) and, because the coil size is independent of the gap width, much larger coils can be used. This yields significantly larger Bl products than equivalently sized moving coil actuators.

Figure 9:
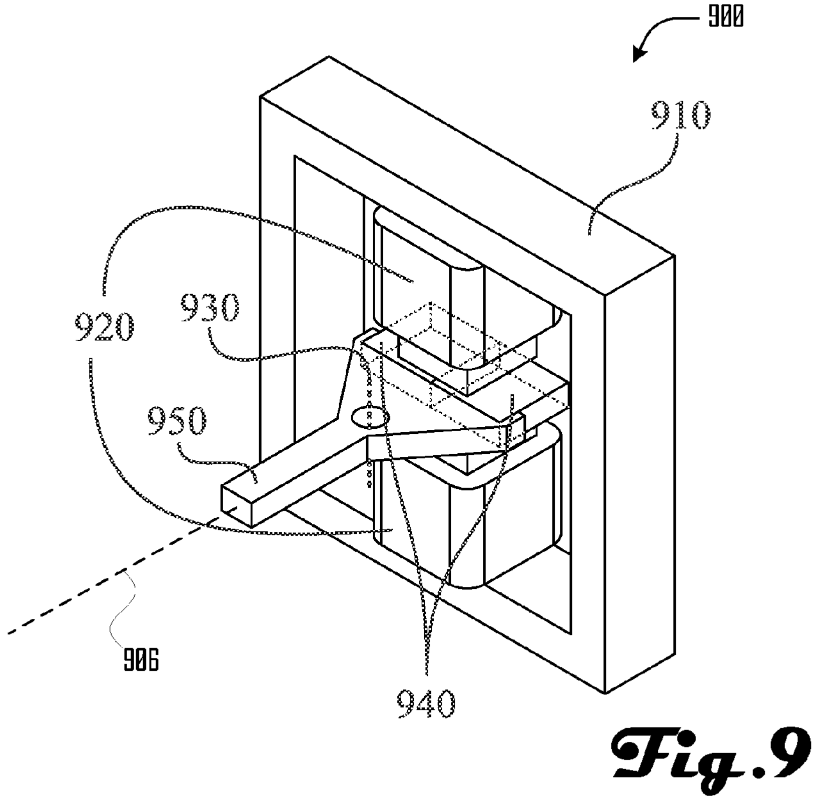

FIG. 9 depicts rotary double-E voice-coil actuator 900, which is similar to actuator 700 (discussed above) but with a different yoke configuration. The yoke 910 has the double E configuration typical of transformers. The two coils 920 flank the gap in the core providing better flux coupling. The stronger magnetic field acts on an opposed permanent magnet pair 940 with the same arrangement as introduced in FIG. 7. This produces a torque about pivot 930 on the arm 950. Pivot 930 is oriented transverse to a longitudinal axis 906 of an elastic body (not shown).

Figure 10:
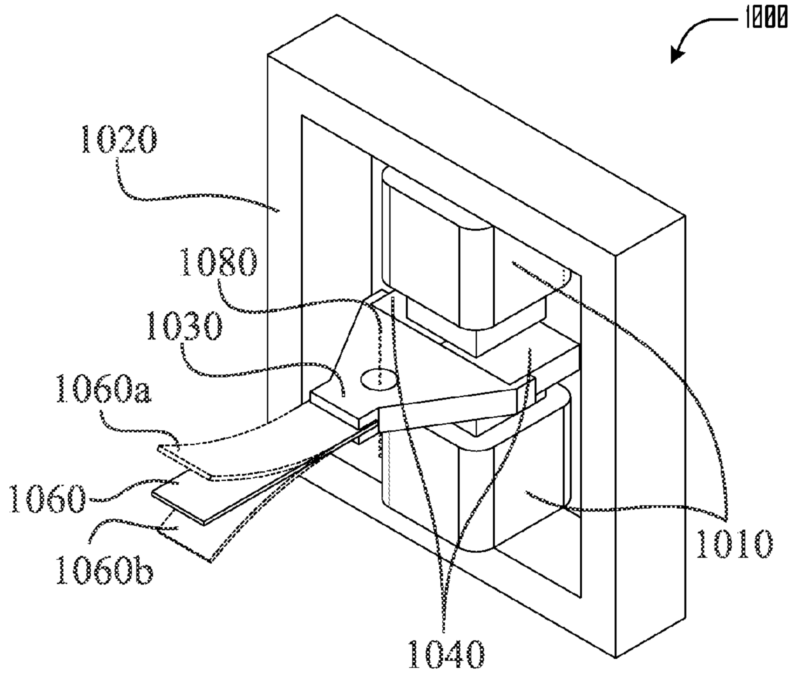

FIG. 10 depicts rotary flexible voice-coil actuator 1000, which is similar to actuator 900 (discussed above), but with an arm 1060 that is flexible perpendicular to the motion of the actuator; deflected arms 1060*a* and 1060*b* represent the deflection up and down respectively of the arm 1060. Other elements are similar, including flanking coils 1010, opposed permanent magnets 1040, double E core 1020, pivot 1080, and rotor-arm-base 1030 and arm 1060 that form the pivot arm assembly. Adding the flexible section to the pivot arm allows the actuator to move relative to the elastic body perpendicular to the actuated motion, which provides additional flexibility without compromising the actuator's ability to couple energy into the elastic body. This can also be achieved by creating a joint in the pivot arm that allows for motion perpendicular to the actuation movement.

Figure 11A:
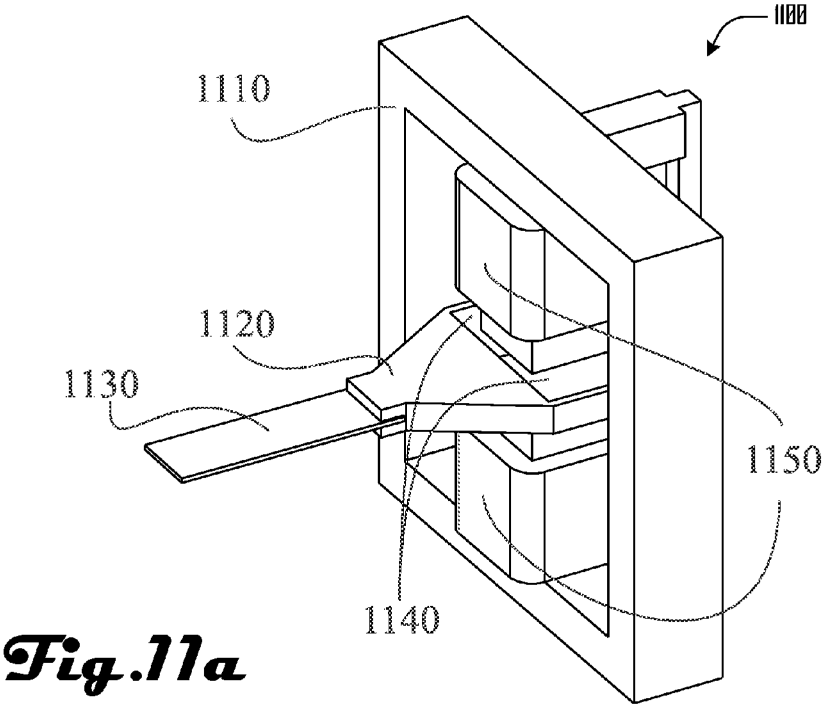
Figure 11B:
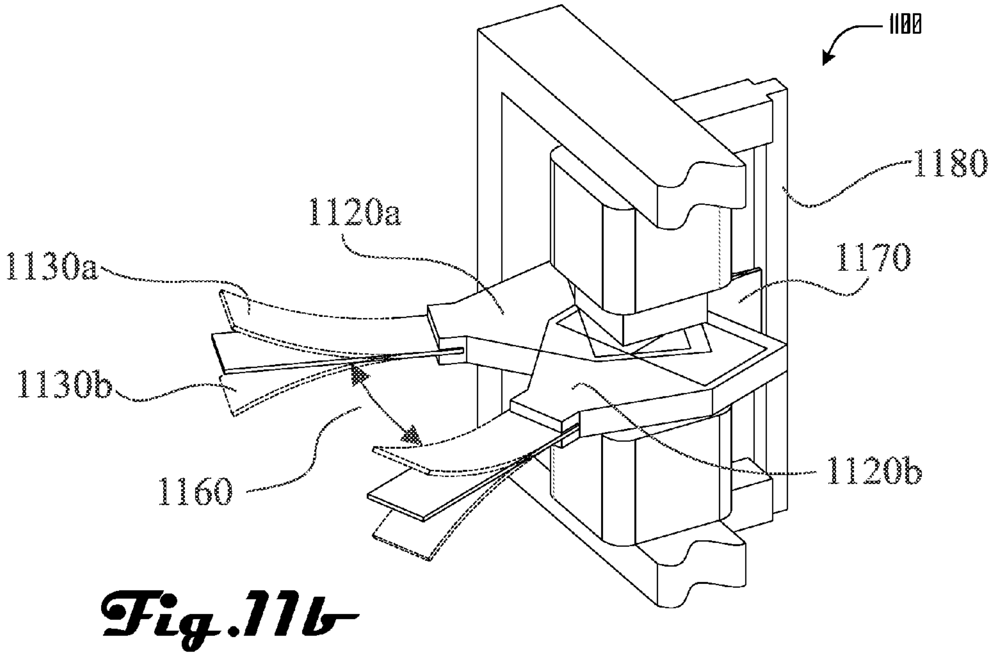

FIG. 11*a* depicts rotary flexure voice-coil actuator 1100, which is similar to actuator 1000 (discussed above), but the pivot is formed by a flexure 1170 on the opposite side of the core. Other elements are similar, including flanking coils 1150, opposed permanent magnets 1140, double E core 1110, rotor-arm-base 1120, and flexible pivot arm 1130. FIG. 11*b* shows a cutaway of the core 1110 so that the flexure 1170 is visible. Displaced arms 1120*a* and 1120*b* show the pivoting motion 1160 of flexure 1170. Additionally, flexible pivot arm 1130 is able to flex up and down as illustrated by displaced arms 1130*a* and 1130*b*. This displacement capability provides flexibility between the actuator and the elastic body (not shown) and limits the amount of vertical force imparted to flexure 1170.

Figure 12A:
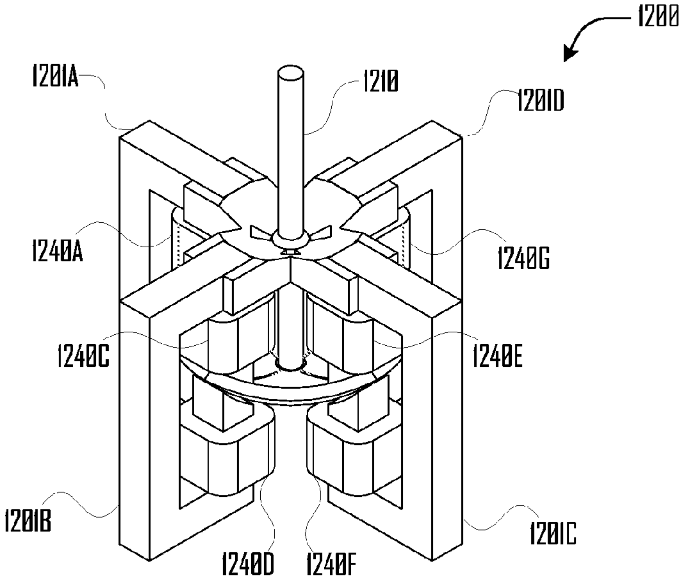
Figure 12B:
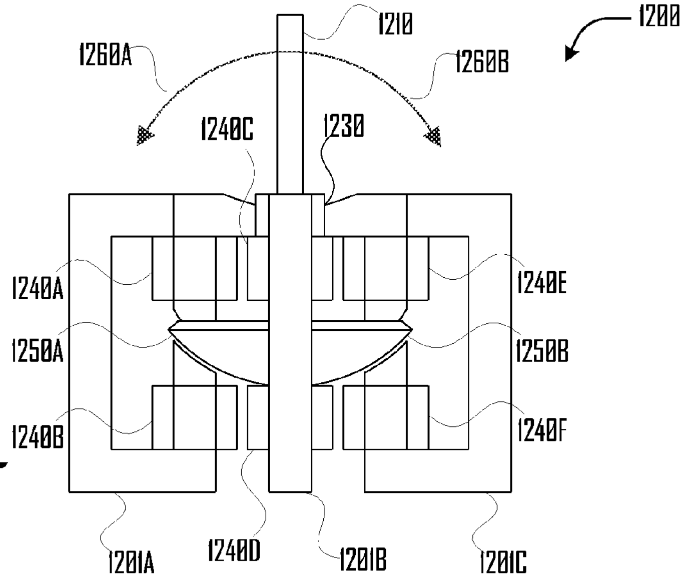
Figure 12C:
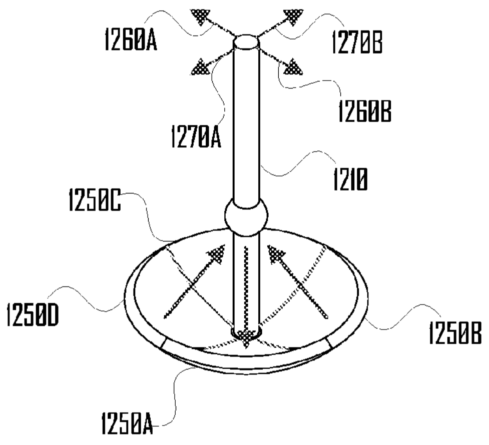

FIGS. 12*a-c* depict rotary multi-dimensional voice-coil actuator 1200, which uses the same principal of operation as actuator 700 (discussed above), but is designed to move in two dimensions. Two-dimensional motion is achieved by using magnets 1250*a-d* that take the shape of a hemispherical shell. FIG. 12*b* depicts the set of spherical magnets 1250*a-b* (1250*c-d* are hidden in this view) and the pivot arm 1210. The spherical magnet assembly is divided into quadrants 1250*a-d*. Each adjacent quadrant has the opposite magnetic polarity. As shown in FIG. 12*c*, magnet 1250*a*'s field points radially outward from the center of the sphere, magnet 1250*b*'s field points inward, magnet 1250*c*'s field points outward, and magnet 1250*d*'s field points inward. This alternating-polarity assembly forms four magnetic junctions with spherical geometry.

FIG. 12*a* shows the same spherical magnet assembly 1250*a-d* and pivot arm 1210 surrounded by four low reluctance magnetic cores 1201*a-d*, one for each magnetic junction. Each of cores 1201*a-d* has a gap flanked by coils 1240*a-g* similar to actuator 900 (discussed above). Actuator 1200 includes eight coils, although only coils 1240*a-g* are visible in FIGS. 12*a-b*. Pivot assembly 1230 holds the cores in place and forms a ball pivot with the pivot arm 1210, which allows the arm 1210 to move freely in two dimensions. Because the magnets 1250*a-d* are spherical and centered at the pivot point and the core gaps are shaped to contour the magnets the pivot and magnets can move freely about the pivot assembly 1230. Arrows 1270*a-b* and 1260*a-b* represent the orthogonal directions the actuator 1200 can move in. Movement is not limited to one dimension at a time. The actuator can move in both dimensions simultaneously. FIG. 12*b* is a side view perpendicular to the 1260*a-b* dimension that shows clearly the hemispherical magnets 1250*a-d* and the contoured magnetic gap. In some embodiments, such a two dimensional actuator can couple energy into an arbitrary transverse orientation of the elastic body.

Figure 13:
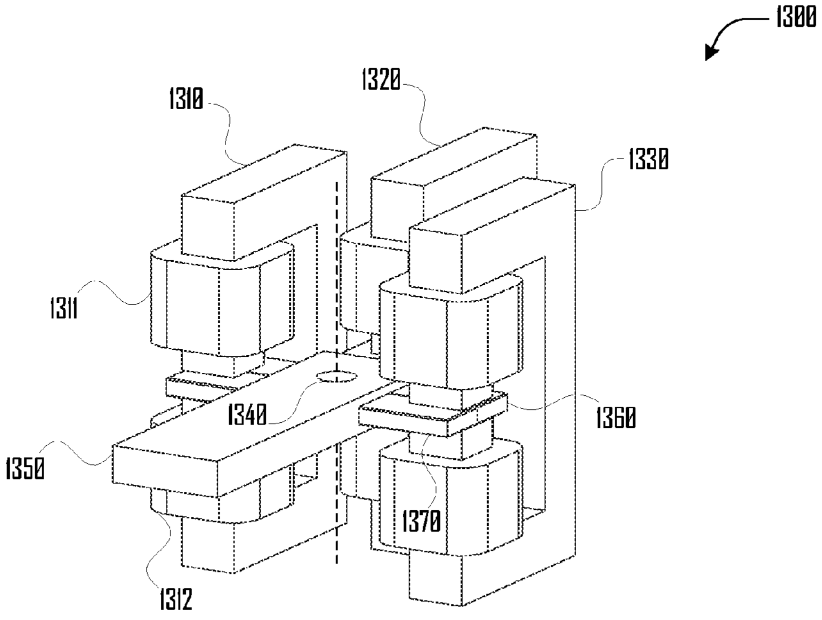

FIG. 13 illustrates multi-core voice-coil actuator 1300, which uses multiple cores in combination to improve torque and efficiency. A single rotor arm 1350 has multiple magnetic junctions arrayed around pivot 1340. Actuator 1300 uses three cores 1310, 1320, and 1330, but other embodiments may use a greater number of cores. Each core has coils, such as coils 1311-1312, flanking the gap and a set of two magnets, such as magnets 1370 and 1360, forming a junction in the gap. In some embodiments, multiple core actuators may provide better flux linkage and performance for some applications and geometries than a single larger coil.

Figure 14:
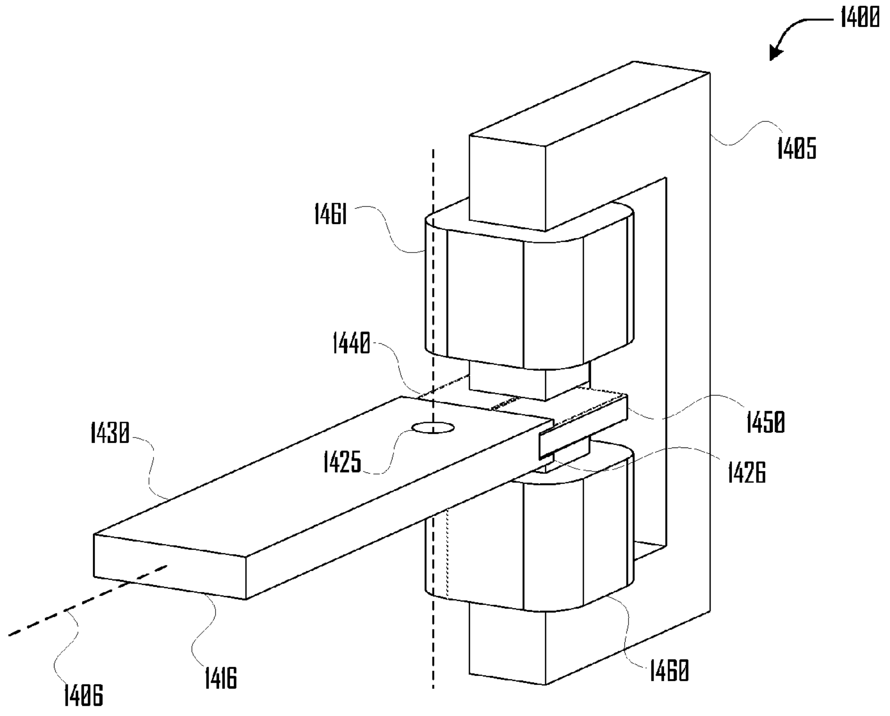

FIG. 14 illustrates rotary single-core voice-coil actuator 1400, which is similar to actuator 1300 (discussed above), but that uses only a single core. In various embodiments, actuator 1400 (like those discussed above) may be used as an actuator in sexual stimulation devices employing torque transducers 400 and/or 500, as discussed above. In some embodiments, such a moving-magnet actuator may be adapted for use as an actuator in torque transducer 600, as discussed above.

Actuator 1400 comprises a core 1405 of low magnetic-reluctance material; a pivot 1425; rotor arm 1430; coils 1460-61; and magnets 1440. The magnetic assembly (including core 1405, coils 1460-61, and magnets 1440) is coupled with the proximal end 1426 of rotor arm 1430 so as to generate, in response to an input current, an oscillating force perpendicular to a longitudinal axis 1406 of an elastic body (not shown). The distal end 1416 of rotor arm 1430 would typically impart the oscillating force into the elastic body via an internal drive surface (not shown) of a hollow bore extending through the elastic body. In some embodiments, the oscillating force may be proportional to the input current.

The "C" shaped core 1405 carries the magnetic field created by the coil 1401 to gap lg creating a magnetic field that is proportional to the current in the coil 1401. Pivot 1425 is oriented transverse to longitudinal axis 1406.

Figure 8:
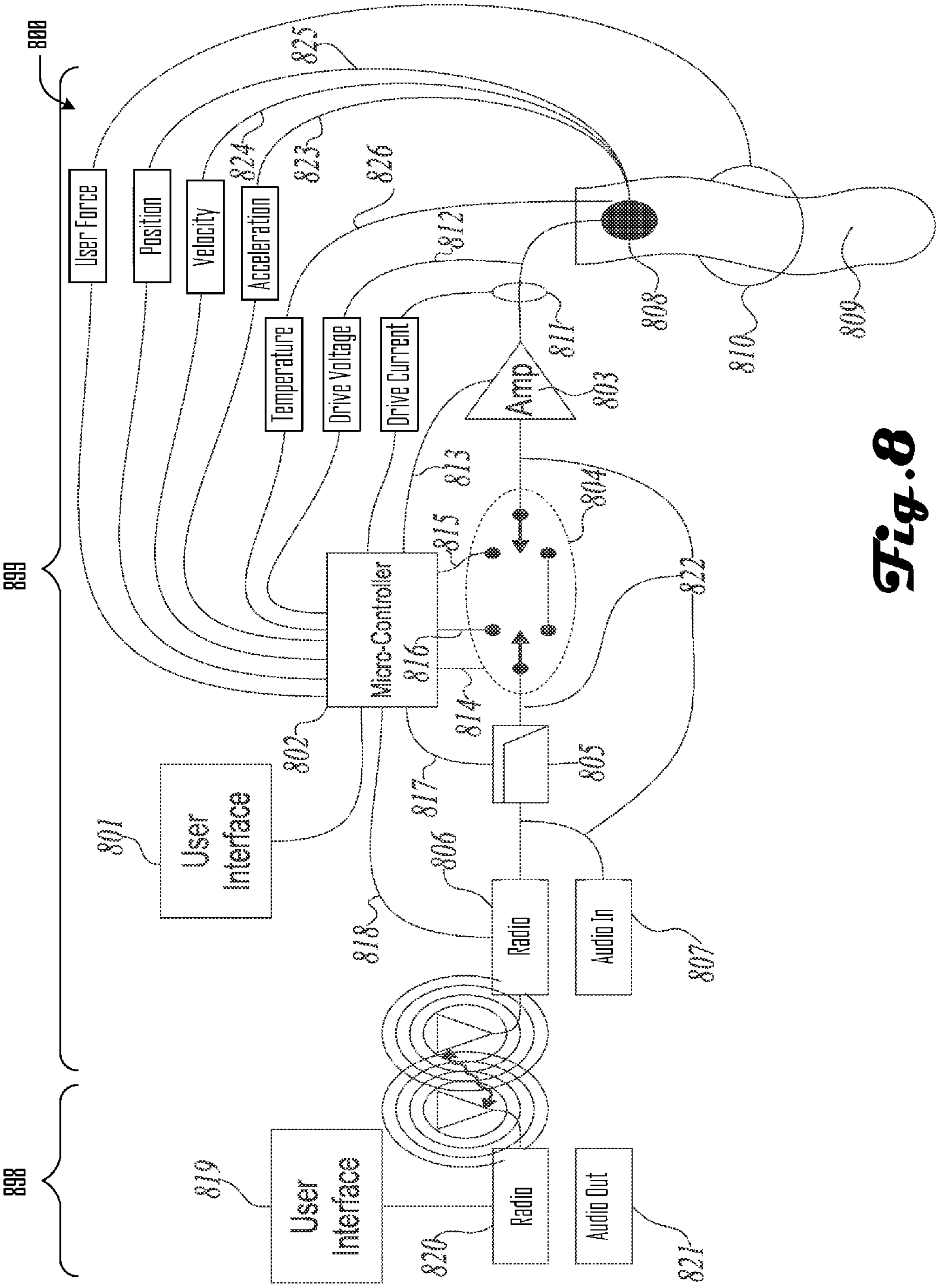
FIG. 8 shows a stimulation-device system, in accordance with one embodiment.

FIG. 8 shows a stimulation-device system 800, in accordance with one embodiment. System 800 includes a remote input device 898, and a stimulation device 899 including four subsections: input, control and processing, current driver, and electrical mechanical transducer system.

Input.

The input subsection includes an RF transceiver 806, which could utilize any suitable wireless standard, such as Bluetooth, zig-bee, xbee, Wi-Fi, and the like; and an electrically-coupled audio input 807, such as a simple waveform phone or headphone style input jack. The input subsection of the primary device receives information and input signal waveforms from the remote input device and/or from the electrically coupled input 807.

Control and Processing.

The control and processing subsection includes a user interface 801, a micro-controller 802, a low pass filter 805, a gating switch 804, and a current probe 811. In various embodiments, user interface 801 may take the form of an LCD, LED, beeper, speaker, or the like. The micro-controller 802 is potentially connected to each of the elements of the system; its role is to control these elements and, depending on the use case, filter and process the input signal waveform through the gating switch before being passed onto the driver subsection.

The current probe 811 provides the micro-controller 802 with a measurement of the current flowing through the actuator 808. The voltage meter 812 provides the micro-controller 802 with a measurement of the voltage across the actuator coil. Using the measurement of the current and voltage, the micro-controller 802 can determine the amount of power being driven into the actuator 808 by the amplifier 803. The micro-controller 802 can set the gain of the driver 803 using control line 813. As a result, the micro-controller 802 can adjust the amount of power that is being driven into the actuator 802. Control line 813 can also be used to control the amplitude of the vibration as dictated by the user through user interface 801 and/or user interface 819.

The gating switch 804 allows the input signal waveform signal line 822 to be diverted to the micro-controller 802 or directly to the driver 803. The analog to digital converter 816 digitizes the signal from the low-pass filter 805 so it can be read into the micro-controller 802. The digital to analog converter 815 reproduces the analog signal for the driver 803. The state of the gating switch 804 can be set by control line 814. The control line 817 is used to set the cut off frequency of the low-pass filter 805. Data line 818 carries data between the micro-controller 802 and the RF transceiver 806.

When the low-pass filter 805 is directly connected to the power amplifier 803, it may remove frequencies that exist in the input signal that are either not perceivable or not desirable by the user. For example, in some embodiments, if spectral content beyond the perception band is amplified and transduced to the primary device, power is wasted in the process and little or no user benefit is produced. Thus, in some embodiments, removing frequencies that are not perceivable by the user may improve system efficiency for signals that contain spectral content beyond the perception band without affecting the user experience. For frequencies that do affect the user experience, either a single compromise cut off frequency is used that is good for most users (one size fits all) or the micro-controller 802 can be used to set the low-pass filter 803 cut off frequency per user input from the user interface. However, in many embodiments, the user may be restricted to settings within the perception band.

When the low-pass filter is connected to the micro-controller 802, and the micro-controller 802, in turn, is connected to the power amplifier, the micro-controller 802 may further shape the waveform by digitizing and further modifying the waveform to provide a more desirable user experience. In some embodiments, In this configuration, the low pass filter's function is to filter out spectral information in the input signal that is greater than the sampling rate of the micro-controller 802 to eliminate erroneous measurements.

In some embodiments, the input signal waveform can be synthesized by the micro-controller 802. In some embodiments, micro-controller 802 may synthesize and/or process an input signal waveform that includes a frequency component that corresponds to a desired mode of vibration in elastic body 809. For example, if elastic body 809 had physical properties similar to that of body 100 (see FIG. 1, discussed above), then in some embodiments, micro-controller 802 may synthesize and/or process an input signal waveform that includes a frequency component of 12 Hz, 76 Hz, 212 Hz, or 416 Hz, which would facilitate elastic body 809 to resonate in its first, second, third, or fourth mode of vibration, respectively. In some embodiments, the desired mode and/or resonant frequency may be indicated via one or both of user interface 801 and 819.

In some embodiments, a temperature sensor 826 monitors the device temperature and feeds it back to the micro-controller 802. This serves at least two functions: one, to establish a maximum safe temperature limit which, if exceeded, the device automatically turns off and, two, the micro-controller 802 can use the device temperature information to control the output power of the amplifier to keep the device within the safe temperature range.

In some embodiments, actuator position 825, velocity 824, and acceleration information 823 can be used by the micro-controller 802 to improve the linearity of the electrical mechanical transducer 808 response and/or in the amplifier 803.

Driver.

The amplifier 803 is a power amplifier, such as of a class A, B, AB, C, D, T, or the like; amplifier 803 supplies the electrical mechanical transducer 808 with an input current that is proportional to the input signal waveform from the control and processing subsection.

Electrical Mechanical Transducer System.

This system is comprised of an elastic body 809 shaped appropriately for the user, an electrical mechanical actuator 808 (e.g., one of actuators 700, 900, 1000, 1100, 1200, 1300, and 1400) that displaces the body 809 proportional to the input current, and a force sensor 810. The role of the transducer system is to transduce electrical signals into mechanical vibrations perceived by the user. Another part of its function is to sense force, or user muscle contraction, on the rod's surface and to relay that information to the microprocessor.

Remote Input Device.

The remote input device transmits waveforms and/or preferences to the stimulation device. It is comprised of an RF transceiver 820, an input jack 821, and a user interface 819. The RF transceiver 820 relays information from the user interface and waveforms from the input jack to the primary device. The radio 820 could use any suitable wireless standard, such as Bluetooth, zig-bee, xbee, Wi-Fi, and the like. The user interface 819 could be an LCD or LED screen, a beeper, a cell phone, and the like. In some embodiments, the audio output 821 is a simple phone or headphone style jack.

Although specific embodiments have been illustrated and described herein, it will be appreciated by those of ordinary skill in the art that alternate and/or equivalent implementations may be substituted for the specific embodiments shown and described without departing from the scope of the present disclosure. For example, various embodiments may include electronics and mechanisms for transmitting and faithfully transducing an arbitrary electrical waveform into the transverse mechanical modes of an elastic rod. The mechanisms may include a moving magnet and pivoted arm that is suspended in the gap of a core of low reluctance material with at least one coil wound on the core, the pivoted arm being connected to an elastic body of cylindrical shape. In some embodiments, the core may be C shaped or double-E shaped. In some embodiments, the pivot arm may be made of material that is flexible in the direction perpendicular to the motion of the actuator. In some embodiments, the pivot of the arm may be provided by a bearing; in other embodiments the pivot on the arm may be formed by a spring flexure. In some embodiments, the mechanisms may include a hemispherical magnet actuator capable of moving in two dimensions simultaneously. This application is intended to cover any adaptations or variations of the embodiments discussed herein.

The invention claimed is:

1. A sexual stimulation device comprising:
- an elastic body comprising a distal end, a proximal end, a body length along a longitudinal axis, and a hollow bore extending from said proximal end along said longitudinal axis of said elastic body for at least a projection distance of less than 50% of said body length, said elastic body exhibiting mechanical resonance at a resonant frequency below 400 Hz that corresponds to a transverse mode of vibration of said elastic body;
- a rotary voice-coil actuator abutting said elastic body at said proximal end so as to facilitate said elastic body to resonate in said transverse mode of vibration in response to an input current, said rotary voice-coil actuator comprising:
  - a transverse pivot that is oriented perpendicular to said longitudinal axis;
  - a rotor arm that pivots about said transverse pivot and projects through said hollow bore for said projection distance so as to mechanically couple a distal end of said rotor arm with an internal drive surface of said hollow bore; and
  - a magnetic assembly that is coupled with a proximal end of said rotor arm so as to generate, in response to said input current, an oscillating force that is perpendicular to said longitudinal axis and proportional to said input current, said oscillating force being imparted into said elastic body via said distal end of said rotor arm and said internal drive surface;
- a controller configured to obtain, generate, and/or process an input signal; and
- a power amplifier that is electrically coupled to said rotary voice-coil actuator, operationally coupled to said controller, and configured to generate said input current according to said input signal.

2. The sexual stimulation device of claim 1, wherein said projection distance is between 20%-25% of said body length.

3. The sexual stimulation device of claim 1, wherein said internal drive surface is positioned near an anti-node corresponding to said transverse mode of vibration to further facilitate said elastic body to resonate in said transverse mode of vibration.

4. The sexual stimulation device of claim 1, wherein said input signal comprises a frequency component corresponding to said resonant frequency to further facilitate said elastic body to resonate in said transverse mode of vibration.

5. The sexual stimulation device of claim 1, wherein said rotor arm is mechanically coupled with said hollow bore only near said distal end.

6. The sexual stimulation device of claim 1, wherein said elastic body is generally rod-shaped.

7. The sexual stimulation device of claim 1, wherein said elastic body is characterized by a tensile modulus similar to that of human soft tissue.

8. The sexual stimulation device of claim 1, further comprising an audio input communicatively coupled with said controller and configured to accept said input signal from an external audio source.

9. The sexual stimulation device of claim 8, wherein said audio input comprises a radio transceiver.

10. A sexual stimulation device comprising:
- an elastic body comprising a distal end, a proximal end, a body length along a longitudinal axis, and a hollow bore extending from said proximal end along said longitudinal axis of said elastic body for at least a projection distance of between 15%-50% of said body length, said elastic body being suitable for at least internal stimulation of a human sexual orifice;
- an actuator abutting said elastic body at said proximal end, said actuator comprising:
  - a transverse pivot that is oriented perpendicular to said longitudinal axis;
  - a rotor arm that pivots about said transverse pivot and projects through said hollow bore for said projection distance so as to mechanically couple a distal end of said rotor arm with an internal drive surface of said hollow bore; and
  - a magnetic assembly that is coupled with a proximal end of said rotor arm so as to generate, in response to an input current, an oscillating force perpendicular to said longitudinal axis, said oscillating force being imparted into said elastic body via said distal end of said rotor arm and said internal drive surface;
- a controller configured to obtain, generate, and/or process an input signal; and
- a power amplifier that is electrically coupled to said actuator, operationally coupled to said controller, and configured to generate said input current according to said input signal.

11. The sexual stimulation device of claim 10, wherein said actuator is a rotary voice-coil actuator in which said magnetic assembly is coupled with said proximal end of said rotor arm.

12. The sexual stimulation device of claim 10, wherein said oscillating force is proportional to said input current.

13. The sexual stimulation device of claim 10, wherein said projection distance is between 20%-25% of said body length.

14. The sexual stimulation device of claim 10, wherein said elastic body exhibits mechanical resonance at a resonant frequency below 400 Hz that corresponds to a transverse mode of vibration of said elastic body.

15. The sexual stimulation device of claim 14, wherein said internal drive surface is positioned near an anti-node corresponding to said transverse mode of vibration to facilitate said elastic body to resonate in said transverse mode of vibration.

16. The sexual stimulation device of claim 14, wherein said input signal comprises a frequency component corresponding to said resonant frequency to facilitate said elastic body to resonate in said transverse mode of vibration.

17. The sexual stimulation device of claim 10, wherein said rotor arm is mechanically coupled with said hollow bore only near said distal end.

18. The sexual stimulation device of claim 10, wherein said elastic body is generally rod-shaped.

19. The sexual stimulation device of claim 10, wherein said elastic body is characterized by a tensile modulus similar to that of human soft tissue.

* * * * *